United States Patent [19]
Imran

[11] Patent Number: 5,404,638
[45] Date of Patent: Apr. 11, 1995

[54] METHOD OF FORMING A FLEXIBLE EXPANDABLE MEMBER FOR USE WITH A CATHETER PROBE

[75] Inventor: Mir A. Imran, Palo Alto, Calif.

[73] Assignee: Cardiac Pathways Corporation, Sunnyvale, Calif.

[21] Appl. No.: 272,944

[22] Filed: Jul. 11, 1994

Related U.S. Application Data

[60] Continuation of Ser. No. 104,738, Aug. 11, 1993, abandoned, which is a continuation of Ser. No. 919,199, Jul. 24, 1992, abandoned, which is a division of Ser. No. 859,054, Mar. 27, 1992, abandoned, which is a continuation of Ser. No. 656,764, Feb. 15, 1991, Pat. No. 5,156,161.

[51] Int. Cl.⁶ .......................................... H01R 43/033
[52] U.S. Cl. ........................................ 29/884; 29/454
[58] Field of Search ............. 29/439, 454, 458, 469.5, 29/874, 884; 128/419 P, 642, 658, 786

[56] References Cited

U.S. PATENT DOCUMENTS

| | | | |
|---|---|---|---|
| 4,481,953 | 11/1984 | Gold et al. | 128/786 |
| 4,547,193 | 10/1985 | Rydell | 128/658 X |
| 4,840,186 | 6/1989 | Lekholm et al. | 128/786 X |
| 4,890,623 | 1/1990 | Cook et al. | 128/642 |

FOREIGN PATENT DOCUMENTS

| | | | |
|---|---|---|---|
| 206248 | 12/1986 | European Pat. Off. | 128/786 |
| 317489 | 5/1989 | European Pat. Off. | 128/786 |

*Primary Examiner*—Peter Dungba Vo
*Attorney, Agent, or Firm*—Flehr, Hohbach, Test, Albritton & Herbert

[57] ABSTRACT

Endocardial mapping and/or ablation system for introduction into a chamber of the heart formed by a wall by passage through a lumen leading to the chamber in the heart having blood therein comprising a catheter probe with proximal and distal extremities and having an elongate tubular member with at least one lumen extending therethrough extending the length thereof and with a distal extremity. A plurality of longitudinally and radially spaced apart electrodes are provided. An expandable device is secured to the distal extremity of the flexible elongate tubular member and is movable between a contracted position and an expanded position. The electrodes are mounted on the expandable device whereby when the expandable device is moved to the expanded position in a chamber of the heart the electrodes are moved into engagement with the wall forming the chamber of the heart in which the expandable device is disposed. An elongate element is coupled to the expandable device for moving the expandable device between the contracted and expanded positions. The expandable device has spaces therein through which the blood can flow when the expandable device is in an expanded position. Leads are in contact with the electrodes and extending through the flexible elongate tubular member. Electrical apparatus is connected to the leads for performing electrical functions with respect to the electrodes.

3 Claims, 6 Drawing Sheets

FIG.-10

METHOD OF FORMING A FLEXIBLE EXPANDABLE MEMBER FOR USE WITH A CATHETER PROBE

This is a continuation of application Ser. No. 08/104,738 filed Aug. 11, 1993, now abandoned, which is a continuation of application Ser. No. 07/919,199 filed Jul. 24, 1992, now abandoned, which is a division of application Ser. No. 07/859,054 filed Mar. 27, 1992, (abandoned), which is a continuation of application Ser. No. 07/656,764 filed Feb. 15, 1991, now U.S. Pat. No. 5,156,161.

This invention relates to an endocardial mapping and ablation system and catheter probe and method.

Endocardial mapping and ablation catheters have heretofore been provided. However, they have been of limited capability particularly because they only have very few electrodes which makes it difficult to map accurately the electrical potentials in the walls forming the chambers of the heart, as for example, the right ventricle. In order to obtain information from several different sites, it has been necessary to maneuver the distal extremity of the catheter extensively and to reposition it radially incrementally in the chamber of the heart. Such a procedure has been found to be time consuming and relatively inaccurate. There is therefore a need for a new and improved endocardial mapping and ablation system and a method for accomplishing the same.

In general it is an object of the present invention to provide an endocardial mapping and ablation system and a method which utilizes a large number of electrodes making it possible to perform endocardial mapping accurately and rapidly.

Another object of the invention is to provide a system and method of the above character in which ablation can be precisely carried out.

Another object of the invention is to provide a system and method of the above character in which bipolar electrode pairs are utilized.

Another object of the invention is to provide a system and method of the above character in which a plurality of radially and longitudinally spaced electrodes are provided which make possible simultaneous measurements through substantially 360° of a wall forming a chamber in the heart.

Another object of the invention is to provide a system and method of the above character in which the electrodes are expanded into engagement with the wall of the chamber of the heart and are maintained in engagement with that wall during pumping action of the heart.

Another object of the invention is to provide a system and method in which the electrodes are yieldably retained in engagement with the wall forming the chamber of the heart during the time that the heart is expanding and contracting the chamber.

Another object of the invention is to provide a system and method of the above character in which a catheter probe is utilized having an expandable distal extremity and in which the distal extremity of the catheter probe is adapted to be disposed in the chamber of the heart.

Another object of the invention is to provide a system and method of the above character in which the presence of the distal extremity of the probe in the heart does not substantially impede the flow of blood in the chamber of the heart.

Another object of the invention is to provide a system and method of the above character in which the mapping and ablation procedures can be carried out without movement of the distal extremity of the catheter probe with respect to the wall forming the chamber of the heart.

BRIEF DESCRIPTION OF THE DRAWINGS

Additional objects and features of the invention will appear from the following description in which the preferred embodiment is set forth in detail in conjunction with the accompanying drawings.

DETAILED DESCRIPTION OF THE DRAWINGS

In general, the endocardial mapping and ablation system of the present invention is utilized for introduction into a chamber of the heart formed by a wall of the heart. It consists of a catheter having proximal and distal extremities. The catheter probe is comprised of a flexible elongate tubular member having at least one lumen therein extending the length thereof and having proximal and distal extremities. A plurality of longitudinally and radially spaced apart electrodes are provided. Expandable means is secured to the distal extremity of the flexible elongate tubular member and is movable between a contracted position and an expanded position. Means is provided for mounting the electrodes on the expandable means whereby when the expandable means is moved to the expanded position in a chamber in the heart, the electrodes are moved into engagement with the wall forming the chamber of the heart in which the expandable means is disposed. Means is coupled to the expandable means for moving the expandable means between said contracted and expanded positions. The expandable means has open spaces between the same so as to permit the flow of blood through the spaces when in the expanded position. Leads are provided which are in contact with the electrodes and extend into the flexible elongate tubular member to the proximal extremities thereof. Electrical means is provided which is connected to the leads for performing mapping and ablation and programed electrical stimulation functions in conjunction with said electrodes.

Figures 1, 7, 8, 9:
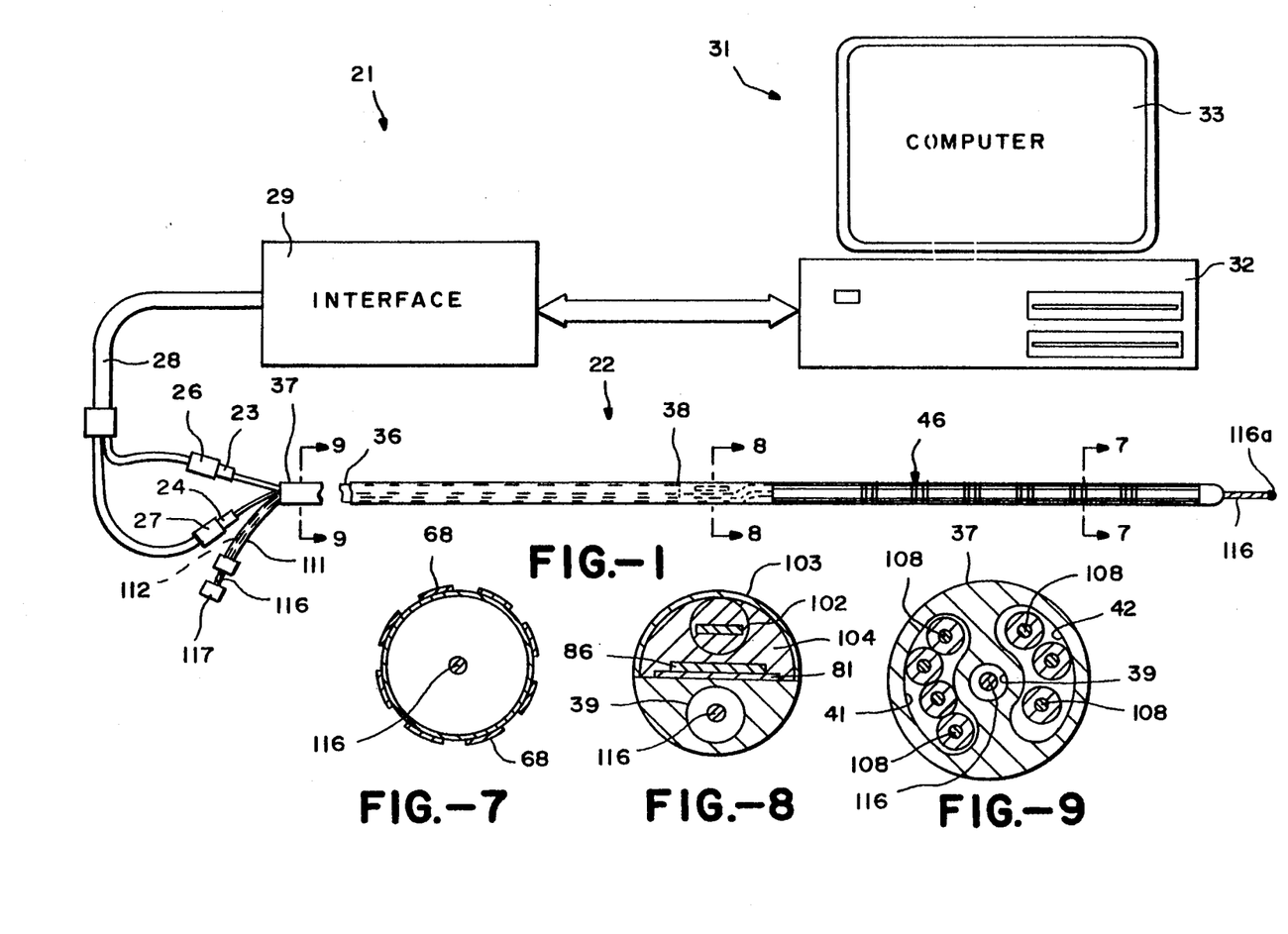
FIG. 1 is a schematic illustration of an endocardial mapping and ablation system and catheter probe incorporating the present invention.
FIG. 7 is a cross-sectional view taken along the line 7—7 of FIG. 2.
FIG. 8 is an enlarged cross-sectional view taken along the line 8—8 of FIG. 2.
FIG. 9 is a cross-sectional view taken along the line 9—9 of FIG. 2.

More in particular, the endocardial mapping and ablation system 21 as shown in the drawings consists of a catheter probe 22 which is provided with a high voltage connector 23 and a signal connector 24 that are connected to mating connectors 26 and 27 forming a part of a cable 28. Cable 28 is connected to a catheter interface module 29 which supplies and receives appropriate signals to and from a computer 31 that is provided with a disc drive 32 and a monitor 33. It is also provided with a keyboard (not shown) for use in controlling the operation of the computer.

The catheter probe 22 consists of a flexible elongate tubular member 36 formed of a suitable material such as plastic which is circular in cross section as shown in FIG. 7. The tubular member 36 has a suitable diameter as for example 0.10" to 0.150" and a suitable length as for example from 100 to 150 cm. The tubular member 36 is provided with proximal and distal extremities 37 and 38 and is provided with at least one lumen and as shown in FIG. 9 is provided with three lumens 39, 41 and 42 in which lumen 39 is a centrally disposed lumen and lumens 41 and 42 are two generally crescent-shaped lumens provided on opposite sides of the lumen 39. Both lumens 39 and 41 extend from the proximal extremity 37 to the distal extremity 38 of the tubular member 36.

A flexible expandable cylindrical member 46 is secured in a fixed position to the distal extremity of the flexible elongate tubular member 36. The expandable cylindrical member 46 is movable between contracted and expanded positions as hereinafter described. The expandable cylindrical member is provided with a plurality of circumferentially spaced apart longitudinally extending flexible arms 47 having adjoined proximal and distal extremities or end portions 48 and 49 (see FIG. 6).

The flexible expandable cylindrical member 46 is formed from a flexible flat sheet 51 (see FIG. 2) which is in the form of an elongate rectangle having sideways extending ears 52 and 53 on opposite ends. The sheet 51 is formed of a suitable insulating material such as plastic. One plastic found particularly suitable is a polyimide identified as Kapton (trademark). Assuming that the plurality of arms 47 to be utilized in the cylindrical member 46 is eight, the sheet 51 is slitted with a knife or die (not shown) to provide parallel spaced apart slits 56 extending longitudinally between the ears 52 and 53 to form the plurality of circumferentially spaced longitudinally extending arms 47. Small holes 57 are provided on the opposite ends of each of the slits 56 and serve to prevent propagation of the 56 slits into the proximal and distal extremities or end portions 48 and 49 of the sheet 51.

In order to impart springiness to the arms, the sheet 51 can be formed of two plastic sheets bonded together over die cut metal strips 61 of a suitable material such as stainless steel or plastic having narrowed portions 61a (see FIG. 3) so that the metal strips 61 are embedded between the two layers 62 and 63 of plastic (see FIG. 4) and encapsulated therein so that they lie in the areas between the lines in which the slits 56 are to be cut. In certain applications of the present invention, it may be desirable to form the strips 61 with a particular pattern to achieve a desired conformation for the bowing out of arms 47 of the expandable cylindrical member 46 when it is expanded as hereinafter described. The narrowed portion 61a can be provided at the proximal extremity to achieve greater bowing of the arm 47 in that region as the cylindrical member 46 is expanded as hereinafter described. The stainless steel strips can have a desired width, as for example, less than the width of the arms 47 and can have a suitable thickness as for example 0.001" to 0.010" in thickness and the plastic layers 62 and 63 can have a suitable thickness ranging from 0.001" to 0.010" in thickness and typically a thickness of 0.002".

Figures 2, 3, 4, 5:
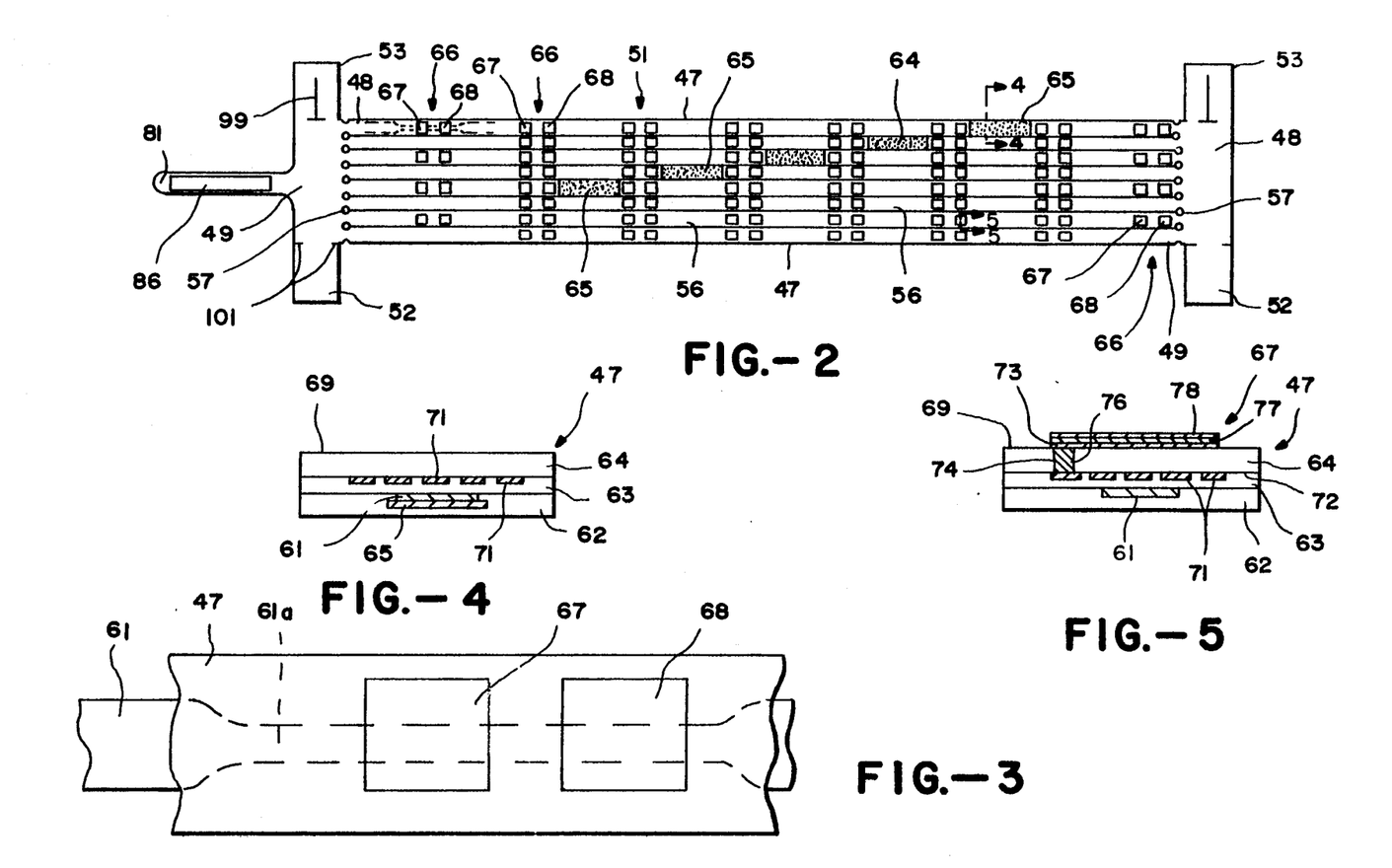
FIG. 2 is an enlarged plan view showing in particular the flexible sheet used to form the cylindrical member at the distal extremity of the catheter probe shown in FIG. 1.
FIG. 3 is an enlarged detail view of a portion of one of the arms of the cylindrical member showing the spring metal strip used in the arm.
FIG. 4 is an enlarged cross sectional view taken along the line 4—4 of FIG. 2.
FIG. 5 is an enlarged cross-sectional view taken along the line 5—5 of FIG. 2.

Radially spaced apart rectangular radiopaque markers 64 formed of a suitable material such as lead or platinum can be positioned so that they underlie the stainless steel strips 61 and are embedded between the layers 62 and 63 of the layers 62, 63 and 64 forming the sheet 51. As shown in FIG. 2, the markers 65 are staggered in distance from the distal extremity so that they form a portion of a helix when the sheet 51 is formed into the cylindrical member 46 as hereinafter described. The markers 65 are only placed on certain of the arms 47 as for example five of the eight arms shown in FIG. 2. This aids in ascertaining the rotational position of the member 46 under flouroscopy as hereinafter described.

Figure 6:
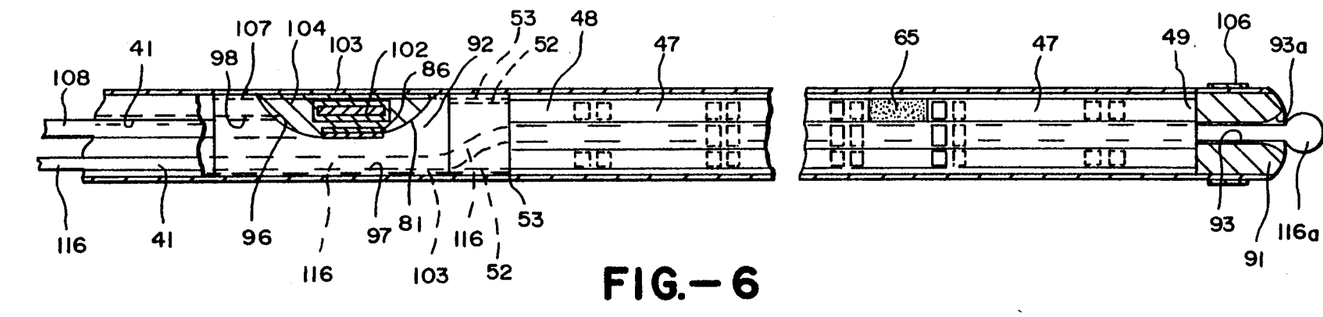
FIG. 6 is an enlarged detail view partially in cross section of the distal extremity of the catheter probe.

A plurality of longitudinally and radially spaced apart sets 66 of bipolar electrodes 67 and 68 are provided on the exterior surfaces 69 of the arms 47 which serve as insulating substrates and are spaced laterally of sheet 51 (see FIG. 6) and circumferentially around the cylindrical member 46 (see FIG. 6). The cylindrical member 46 serves as an expandable means secured to the distal extremity of the tubular elongate element 36 and is movable between contracted and expanded positions whereby when the expandable means is moved to the expanded position the electrodes 67 and 68 are brought into engagement with the wall of the heart forming the chamber in which the expandable means is disposed as hereinafter described.

The electrodes 67 and 68 as shown are rectangular in shape and can have a length of 0.040" and a width of 0.040". The bipolar electrodes 67 and 68 can be separated by a suitable distance as for example 0.040". If desired the electrodes 67 and 68 can be of different sizes. Leads 71 are provided on the interior or inner surfaces 72 of the arms 47. The electrodes 67 and 68 and the leads 71 are formed of a suitable conductive materials. The outer or exterior surfaces 69 and the inner or Anterior surfaces 72 of the arm 47 of sheet or substrate 51 are coated with vapor deposited or electroplated layer of a suitable conductive metal such as copper to provide a copper layer 73 of a suitable thickness as for example 0.0005". The sheet 51 is then drilled to form holes 74 extending between the copper layers 73. Additional conductive material such as copper is then plated through the holes 74 to form the vias 76 (see FIG. 5). Thereafter, conventional etching techniques are used to remove the undesired copper material on the outer surfaces 69 and on the inner surfaces 72 of the arms 47 so that there remains longitudinally spaced apart electrodes 67 and 68 on the outer surface 69 and laterally spaced apart longitudinally extending leads 71 which are connected to the sets 66 of electrodes 67 and 68 by the vias 76. Each of the electrodes 67 and 68 is connected to one of the leads 71 by a via 76. The leads 71 are insulated from the metal strips 61 by the plastic layer 63.

The electrodes 67 and 68 as well as the leads 71 can be augmented by plating onto the copper layer 73. Thus, as shown in FIG. 5, the electrode 67 can be augmented by depositing a nickel layer 77 on the copper layer 73 followed by a gold layer 78 deposited on the nickel layer 77. Gold is particularly suitable as a final layer in this application because it is inactive in blood. It also is an excellent conductor.

The proximal end of the sheet 51 shown in FIG. 2 is provided with an extension 81. A multiplexer chip 86 of the type hereinafter described is mounted on or attached to extension 81 by conventional bonding techniques and is connected by conventional techniques to the leads 74 connected to the electrodes 67 and 68.

In forming the sheet 51 of FIG. 2 into the cylindrical member 46, a distal mandrel 91 and a proximal mandrel 92 are utilized. The distal mandrel 91 is cylindrical in form and can be formed of a suitable material such as plastic or metal. The distal mandrel 91 is provided with a centrally disposed hole 93 which is provided with an outwardly flared portion 93a. The proximal mandrel 92 is also formed of a suitable material such as plastic and is provided with a cup-like recess 96 (see FIG. 6). It is also provided with a hole 97 which curves slightly downwardly to clear the recess 96 and extends through the mandrel 92. An additional hole 98 is provided in the mandrel 92 which opens into recess 96.

The sheet 51 is wrapped into a cylinder with the ears 52 overlapping the ears 53 by inserting the ears 52 through T-shaped slots 99 formed in the ears 53 and having pairs of spaced-apart slits 101 mating with the slots 99 so that the outer side margins of the sheet 51 are brought together to form another slit 56 between the two adjacent arms 47. The ears 52 and 53 also can be overlapped and fastened together on themselves by suitable means such as an adhesive. When fabricated in this manner, the cylindrical member 46 typically would have a diameter of approximately 0.150" and a suitable length as for example 2 ½" depending upon the size of the cavity in the heart to be mapped.

During wrapping of the ears 52 and 53 around the mandrel 91, the extension 81 and the chip 86 thereon is positioned within the cup-shaped recess 96. An encased crystal 102 is also mounted in the recess 96 overlying the chip 86. An RC oscillator (not shown) on the chip 86, may be used in place of crystal 102. The recess 96 is enclosed by semi-cylindrical cover 103. Prior to the placement of the cover 103, the chip 86 and the crystal 102 may be encapsulated in a suitable epoxy 104 placed in recess 96. The epoxy 104 can have heat sinking capabilities to dissipate any heat generated within the chip 86.

Figures 13, 14, 15:
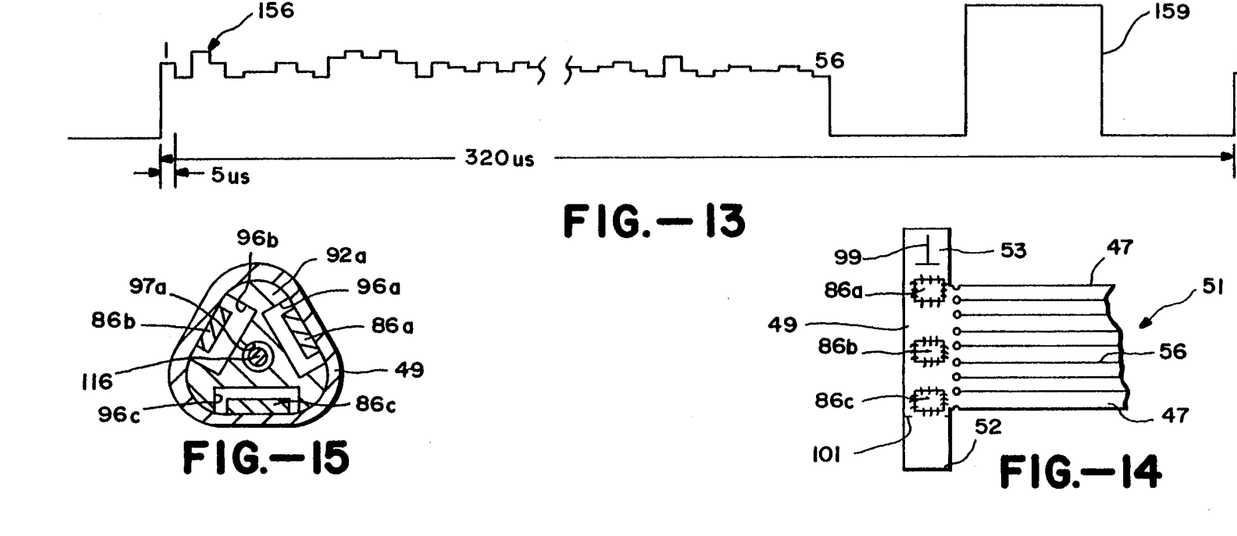
FIG. 13 is a timing diagram for the circuitry shown in FIG. 10.
FIG. 14 is a partial view of another sheet incorporating the present invention for use with a catheter probe which shows a plurality of chips carried thereby.
FIG. 15 is a cross sectional view of a catheter probe showing the manner in which the plurality of chips shown in FIG. 14 are radially disposed about a mandrel for the catheter probe.

An alternative embodiment for the mounting of the multiplexer chip 86 is shown in FIGS. 14 and 15. As shown therein, the multiplexer chip 86 instead of being in only a single package as shown in FIGS. 2 and 6 can have its circuitry as well as other circuitry supplied in a plurality of chips, as for example, chips 86a, 86b and 86c which are mounted on the sheet 51 on the proximal end portion 49 immediately adjoining the ears 52 and the proximal extremities of the arms 47 so that the leads carried by the arms and connected to the electrodes 67 and 68 can be connected directly to the chips 86a, 86b and 86c. Chips 86a, 86b and 86c are spaced apart a suitable distance so that when the sheet 51 is wrapped about the proximal mandrel 92a shown in FIG. 15, the chips 86a, 86b and 86c are received within circumferentially spaced-apart recesses 96a, 96b and 96c provided in the proximal mandrel 92a. Such an arrangement has an advantage in that it makes it possible to provide additional circuitry if desired in the flexible elongate member 36 in close proximity to the electrodes 67 and 68. Also it permits the hole 97a (see FIG. 15) to be centrally disposed in the proximal mandrel 92a so that the pull wire 116 (hereinafter described) extending therethrough can extend along the center axis of the mandrel 92 rather than being offset as shown in FIG. 6.

A band 106 formed of a suitable conducting metal such as gold is provided at the distal extremity of the cylindrical member 46 over the mandrel 91 and serves as a ground. Alternatively, a large surface area electrode may be placed on the chest of the patient (not shown) to serve as a ground for the ablation current. A tubular sleeve 105 is fitted over the proximal mandrel 92 and extends over the proximal extremity of the cylindrical member 46. The sleeve 103 can be formed of a suitable material such as injection molded plastic. It can be formed as a separate sleeve or can be formed integral with the flexible elongate tubular member 36 forming the probe catheter 22 to provide a one-piece construction.

With respect to the embodiment shown in FIGS. 1–9, the tubular member 36 is rotationally aligned so that its central lumen 39 is in alignment with the hole 98 in the proximal mandrel 92. Because of the multiplexing capabilities of the chip 86 a relatively small number of wires or conductors 108 are connected to the chip 86. For example, as few as seven insulated conductors 108 can be provided which are bonded to pads (not shown) connected to the chip 86. The conductors 108 extend through the hole 98 and into the crescent-shaped lumens 41 and 47 provided in the flexible elongate member 36. The conductors 108 extend through the flexible elongate cylindrical member 36 and are connected to the connectors 23 and 24 heretofore described.

Seven conductors 108 would be provided when bipolar mapping and ablation is desired. Rather than using a single connector for all of the wires or conductors 108, it is desirable to separate the conductors into a high voltage set of conductors and a signal set of conductors.

Thus, with seven conductors, the four conductors associated with high voltage can be connected into the quadrapole connector 23 and the three wires of the signal set can be connected into a triaxial connector 24.

Another tubular member 111 is connected to the proximal extremity 37 of the tubular member 36 and is provided with a lumen 112 which is in registration with the central lumen 39 provided in the tubular member 36. An elongate pull wire 116 is disposed in the lumens 112 and 39 and is formed of a suitable material such as stainless steel and can have a size as for example 0.014" in diameter. The pull wire 116 extends the length of the tubular member 36 and extends into the lumen 97 provided in the proximal mandrel 92 and then into the interior of the flexible expandable cylindrical member 46 which also may be called a cylindrical expandable electrode array and through the hole 93 provided in the distal mandrel 91. After the pull wire or element 116 has been inserted into the catheter and through the hole 93 of the mandrel 91, the distal extremity of the pull wire or element 116 is provided with an enlarged portion 116a which can be formed integral with the pull wire or element 116 or can be formed as a separate part bonded to the distal extremity of the pull wire. The portion 116a has a size which is sufficiently great so that it cannot be pulled through the hole 93 but which is still small enough to seat within the flared portion 93a of the hole 93 and not protrude substantially beyond the distal extremity of the mandrel 91. The pull wire 116 is provided with a knob 117 on its proximal extremity for operation of the pull wire.

Operation and use of the catheter or probe 22 in connection with the catheter interface module 29 and the computer 31 of the system 21 may now be briefly described as follows in utilizing the present invention. The catheter probe 22 is first used with the cylindrical expandable member or electrode array 46 in its normal contracted position which can be ensured by pushing on the knob 117 to fully extend the pull wire 116 to extend beyond the mandrel 91 so that it can serve as guide wire. The catheter or probe 22 is inserted into a cavity 131 of the heart 132 (FIG. 11) as for example the right ventricle of the heart in a human body by access through a femoral vein. This can be accomplished in a conventional manner by introducing the guide wire or pull wire or element 116 and thereafter the distal extremity of the catheter probe 22 into the femoral vein by the use of a guide sheath and/or a guiding catheter. This can be done in a conventional manner under fluoroscopy in which the catheter or probe 22 can be introduced through the superior inferior vend cava into the right atrium and then advanced into the right ventricle as shown particularly in FIGS. 11 and 12. In connection with this procedure, the pull wire 116 can be utilized as a guide wire and can be rotated by rotating the knob 117 to facilitate advancing the catheter through the desired path into the vessel lumen leading to the heart.

Figure 11:
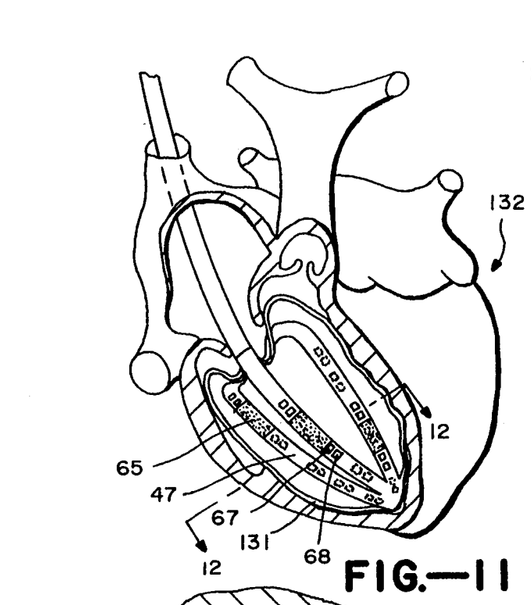
FIG. 11 is a cross-sectional view of the heart showing the manner in which the system and catheter probe of the present invention are employed in the right ventricle to achieve mapping and/orablation in accordance with the method of the present invention.
Figure 12:
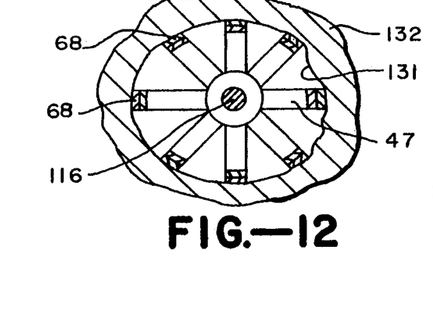
FIG. 12 is a cross-sectional view taken along the line 12—12 of FIG. 11.

As soon as the distal extremity of the catheter probe 22 is positioned within the desired cavity of the heart as for example the right ventricle 131 of a heart 132 as shown in FIG. 11, connectors 23 and 24 can be interconnected with the mating connectors 26 and 27 so that the catheter probe 22 is connected to the catheter interface module 29 and the computer 31. Once this has been accomplished, the pull knob 117 can be retracted to move the portion 116a of the pull wire into the recess 93a and upon further pulling movement to cause expansion of the cylindrical expandable member or electrode array 46 to cause its arms 47 to be bowed outwardly as shown in FIG. 11 with the distal extremity or tip of the cylindrical electrode array 46 touching the distal extremity or apex of the right ventricle 131 so that the arms and the electrodes 67 and 68 carried thereby are brought into contact with the wall of the heart forming the right ventricle. As shown in FIG. 11, the bowing of the arms 47 is more pronounced at the proximal extremity 48 and at the distal extremity 49 of each of the arms 47. This increased bowing is made possible by providing the narrowed portions 61a on the proximal and distal extremities of the metal strips 61 as hereinbefore described. The flexibility of the arms 47 permits the heart to continue its normal beating pattern in moving the wall forming the right ventricle 131 inwardly and outwardly. At the same time because the arms 47 are spread or spaced apart as they are bowed outwardly, there is ample space between the arms so that normal blood flow in the right ventricle 131 can occur substantially unimpeded by the electrode array 46 when the array 46 is in the chamber. The springiness of the arms 47 is such that the arms 47 will yieldably follow the muscular contractions and expansions of the right ventricle and keep the bipolar electrodes 67 and 68 in substantially continuous contact with the heart wall and the electrical circuitry provided in the heart wall. It should be appreciated that similar procedures can be used for positioning the catheter probe 22 in other chambers of the heart as for example the left ventricle of the heart.

In the embodiment shown in FIGS. 1–13, eight arms 47 are provided with six sets of electrode pairs with four of the arms having an additional sets of each end each for a total of 112 electrodes and 56 electrode pairs. Fewer bipolar pairs are provided at the ends because the arms 47 are closer together at the ends when the cylindrical expandable member 46 is expanded. Each bipolar electrode pair is connected to a differential amplifier 141 (see FIG. 10). Each of the differential amplifiers 141 is provided with input circuitry 142 which consists of current limiting resistors R1 and R2 connected to diodes D1 and D2 on opposite sides of the input line with the diode D2 being connected to ground and diode D1 being connected to a positive voltage. Diodes D3 and D4 are connected to the other input line with diode D4 being connected to ground and diode D3 being connected to the positive voltage. These serially connected diodes serve to protect the inputs to the amplifiers 141 during the time that ablation voltages are being applied as hereinafter described. The input circuitry has the capability of limiting the voltage rise at the inputs of the amplifier 141 to approximately ½ volt. The differential amplifiers 141 have a suitable gain as for example typically between 100 and 500. Since the endocardial signals that are received from the heart are of relatively high amplitude, a very high gain is not required from the amplifiers 141.

Figure 10:
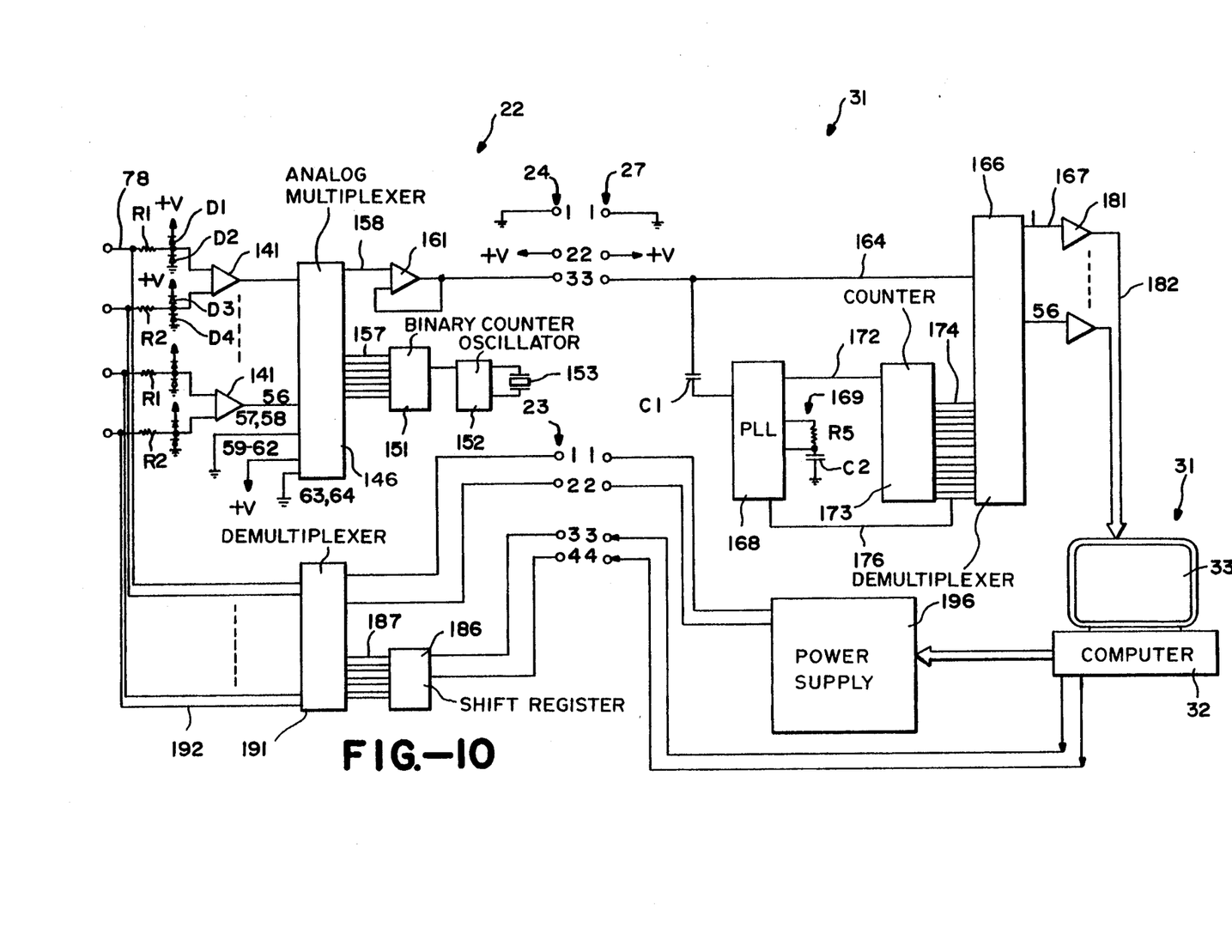
FIG. 10 is a schematic diagram of the electronic circuitry utilized in the system for performing the method of the present invention.

The outputs of the amplifiers 141 are connected by 56 lines 142 identified from 1 to 56 to an analog multiplexer 146. The multiplexer 146 can have a suitable number of inputs as for example 64 inputs as shown. Inputs 1–56 are connected to the cylindrical expandable member 46. Inputs 57–58 can be grounded as shown. Inputs 59–62 can be connected to a positive voltage supply and inputs 63–64 are connected to ground. One or two of these inputs can be utilized for providing a synchronization signal for demultiplexing as hereinafter described.

The multiplexer 146 is driven by a 6 bit binary counter 151 which is supplied with a clock frequency from an oscillator 152 that is controlled by crystal 153 of a suitable frequency as for example, 200 KHz. The 200 KHz oscillator frequency provides a five microsecond cycle length per channel as shown in the waveform. The counter 151 supplies an output 156 shown in FIG. 13 on six lines 157 to the multiplexer 146. The multiplexer 146 is provided with an output 158 which is controlled by the binary counter 151 so that the output from each of the amplifiers 141 appears on the line 158 for the five microsecond pulse length provided by oscillator 152. In the FIG. 13, waveform 156 shows information being received on 56 channels with each channel having a 5 microsecond duration followed by a synchronizing pulse 159 which is 20 microseconds wide to complete one cycle of the multiplexer of 320 microseconds of 146 followed by the next 320 microsecond cycle. This provides an effective sampling rate of about 3000 samples per second.

The output 158 is connected to a buffer amplifier 161 which provides its output on pin 3 of the connector 24. The other pins 1 and 2 of the connector 27 are connected to ground and a plus voltage respectively. The pins 1 and 2 in the connector 24 are connected to ground and a plus voltage respectively in the interface module 17.

Thus the power for the chip 86 is supplied from the interface module 17 through pins 1 and 2 of the connector 27. Pin 3 in the connector 14 receives the output signal from pin 3 of the connector 24 and supplies it through a line 164 to a demultiplexer 166. The demultiplexer 166 is provided with a plurality of output channels 167. Assuming there are 64 input channels in the multiplexer 146, there would be a corresponding number of output channels in the demultiplexer 166.

The information on the line 164 containing the synchronizing signal is also supplied through a capacitor C1 to a phase locked loop (PLL) 168 and is connected to an RC filter network 169 consisting of a resistor R5 an a capacitor C2 connected to ground. The PLL 168 is provided with an output line 172 and has provided thereon a reconstructed 200 Khz voltage controlled oscillator output which is supplied to a counter 173. The counter 173 is provided with a plurality of output lines 174 which are connected to the demultiplexer 166. The lines 174 are provided with frequencies ranging from 100 KHz to 3.125 KHz with the 3.125 KHz line 174 being connected to the phase lock loop 168 by a line 176 which serves to couple the VCO output to the phase lock loop. The use of teh PLL allows the reconstruction of the 200 KHz clock, which is synchronized to the 200 KHz clock 152 in the catheter chip 86.

The demultiplexer 166 serves to demultiplex the information supplied from the multiplexer 146 and supplies it on the 56 channels 167 to circuitry 181 which includes sample and hold circuitry, filter circuitry and A–D converters to provide an output on lines 182 in the form of a signal which is supplied to the computer 31 and to the display monitor 33. The computer 31 is provided with software which has the capability of analyzing information being supplied to it by utilizing sampling techniques well known to those in the art. The computer 31 performs an analysis on the information and by use of propagation and delay time analysis identifies and isolates the area within the ventricle which may contain a re-entry pathway which may need to be ablated. This information is displayed on the screen of the monitor 33 so that it can reviewed by the physician so that the physician can make a decision as to whether or not ablation is desirable.

Let it be assumed that re-entry pathway has been located and it is desired to ablate the same. After the mapping has been accomplished by use of the catheter or probe 22 as hereinbefore described, the same catheter or probe 22 while still in place within the ventricle may be used for accomplishing the ablation. The attending physician inputs the desired commands to the keyboard (not shown) connected to the computer 31 to give the command to proceed with an ablation. As soon as such a command is received by the computer 31, the computer 31 sends a channel number serially to pin 3 of the connector 26 which is connected to the corresponding pin 3 of the connector 23 in a serial to parallel shift register 186 which is disposed in the catheter probe 22. The shift register 186 supplies the channel number to the demultiplexer 186 on the six lines 187 to a high voltage demultiplexer 191. The shift register 186 is provided with a clocking signal on pin 4 of the connector 23 which is supplied with a clock signal on the corresponding pin 4 of the connector 26 from the computer 31.

The output of computer 31 is also connected to a high voltage ablation power supply 196 which is programmable as to channel number and to the amount of energy to be supplied on the channel and supplies its output to pins 1 and 2 of the connector 26 which is connected to corresponding pins 1 and 2 of the connector 23 which are connected to the demultiplexer 191. The high voltage demultiplexer 191 is provided with high voltage transistors which can tolerate the ablation voltages supplied by the power supply 196. Upon command, the ablation power supply 196 supplies a high voltage, high frequency (typically 50–100 volts at 750 KHz to 1 MKz) pulse across the pins 1 and 2 of connector 26. This high voltage pulse appears on the corresponding pins 1 and 2 of the connector 23 and is supplied by the demultiplexer 191 to the appropriate channel and appropriate electrode pair through lines 192 connected to the leads 74. This pulse appears across the electrode pair and causes an ablation to occur in the tissue of the wall of the right ventricle between the electrode pair. Alternatively, ablation can be accomplished between one of the electrode pairs and an external ground electrode placed on the chest of the patient. In this manner, it can be seen that a highly controlled ablation is provided which is precisely positioned with respect to the selected electrode pair.

Several milliseconds after the ablation pulse has been supplied to the appropriate electrode pair, mapping can again be resumed in the manner heretofore described to ascertain whether or not a re-entry pathway is still present. If the mapping indicates that at least a portion of the re-entry pathway is still present, high voltage pulses can be programmed by the computer and supplied to other appropriate electrode pairs until the re-entry pathway has been destroyed. From the pattern of the electrodes provided by the electrode array 46, it can be seen that a compact multiple electrode grid-like pattern is provided having electrode pairs precisely located throughout the entire surface of the wall of the heart forming the chamber in which the elelctrode array 46 is disposed so that ablation can be precisely controlled.

Programmed stimulation can be performed by using a selectable number of electrodes. In this mode of operation the interface 29 provides a programmable level of low voltage pulses (5-10 volts) via the high voltage line to stimulate the heart with synchronized pulses in order to induce or convert an arrythmia.

The staggered radiopaque markers 65 can be utilized to ascertain which of the arms 47 of the expandable member 46 is located closes to the anatomical point of interest in the heart cavity as for example the bundle of His. By observing this staggered relationship of the markers 65, the physician can select the signals coming from a specific arm 47 to analyze the same in the computer 31 to thereby ascertain the condition of the bundle of His.

The staggered relationship of the markers 65 also makes it possible for the attending physician to observe the amount of rotation which occurs in the expendable member 46 when it is rotated by rotation of the proximal extremity of the catheter probe 22. For example, since only five of the markers 65 are used on the right arm which are spaced circumferentially by 45° it is readily ascertainable whether rotatin of 45° has occured or more or less. If rotation of 45° has occured, a marker 65 will be shifted to a different staggered position to the other side of the expandable member 46 which will be in registration with an arm 47. If rotation of less than 45° has occured, the offset marker 65 will not be in alignment with one of the armks 47.

By providing an additional lumen in the catheter which is commonly accomplished in catheters and having that lumen open through a port into the right ventricle, it is possible to measure the pressure in the right ventricle during mapping or ablation. By measuring the pressure in the right ventricle, it is possible to ascertain when the ventricle is filled with blood or whether it is being squeezed. The timing of the ablation can be such that ablation occurs when the ventricle is squeezed to its smallest size. This may be desirable because at this point there will be the best contact between the electrode array 46 and the heart wall forming the ventricle. In addition, it is desirable to carry out the ablation at this point in time because at that time that the amount of blood in the ventricle is at a minimum. Thus, more of the energy created by the ablation pulse is dissipated into the heart wall rather than into the pool of blood in the right ventricle. Also, in order to accomplish this, a pressure transducer 201 can be provided in the cylindrical member or electrode array 46 and connected to electrical wires not shown into the multiplexer 146.

In accordance with the present invention, it can be seen that catheter probe 22 can be provided with an increased number of electrodes if desired. Additional channels can be readily provided in the multiplexer 146 and demultiplexer 166. The shape of the electrode array 46 can be made so that it conforms to the wall of the heart as it expands and contracts through the entire cardiac cycle. This is made possible because of the springiness of the individual arms 47 of the expandable member 46. Intimate contact is maintained with the wall of the heart minimizing the amount of energy which is dissipated into the blood pool within the cavity of the heart during ablation.

With the catheter, system end method of the present invention, mapping and ablation procedures can be carried out within relatively short periods of time, as for example, as little as one half hour. The construction of the catheter is such that it will not interfere substantially with the cardiac output of the heart. It should be appreciated that if desired, ablation can be accomplished with a separate catheter or device. It should also be obvious that if desierd the system may be used to perform a routine electrophysiology study on a patient utilizing the programmed stimulation and mapping features of system.

Another embodiment of a catheter probe incorporating the present invention is shown in FIGS. 16–20. As shown therein, the catheter probe 211 which consists of a flexible elongate tubular member 36 very similar to the flexible elongate tubular member 36 hereinbefore described in the previous embodiment.

Figure 16:
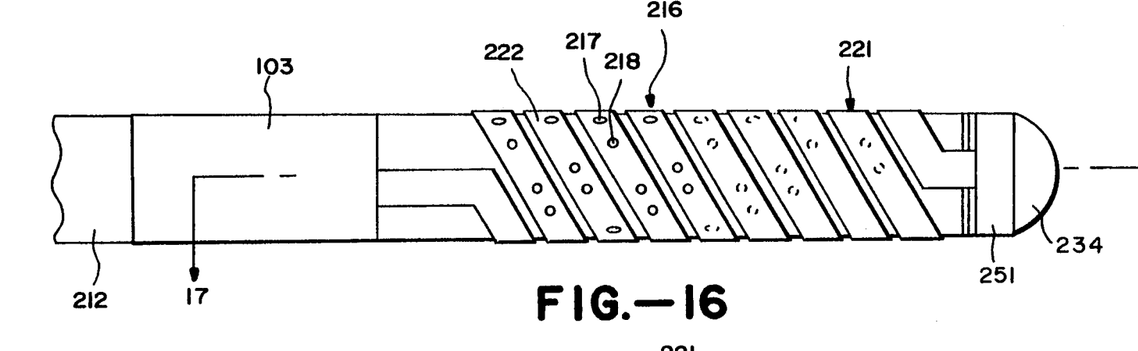
FIG. 16 is a partial plan view of another catheter probe incorporating the present invention and for use with the system and method of the present invention.
Figures 18, 20, 21:
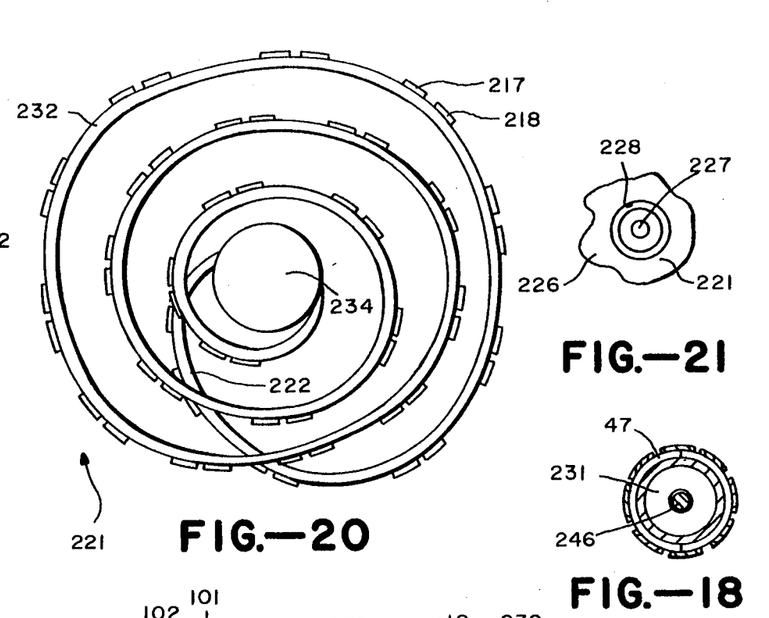
FIG. 18 is a cross sectional view taken along the line 18—18 of FIG. 17.
FIG. 20 is a cross-sectional view taken along the line 20—20 of FIG. 19.
FIG. 21 is a plan view of an alternative bipolar electrode for use with the present invention.
Figure 19:
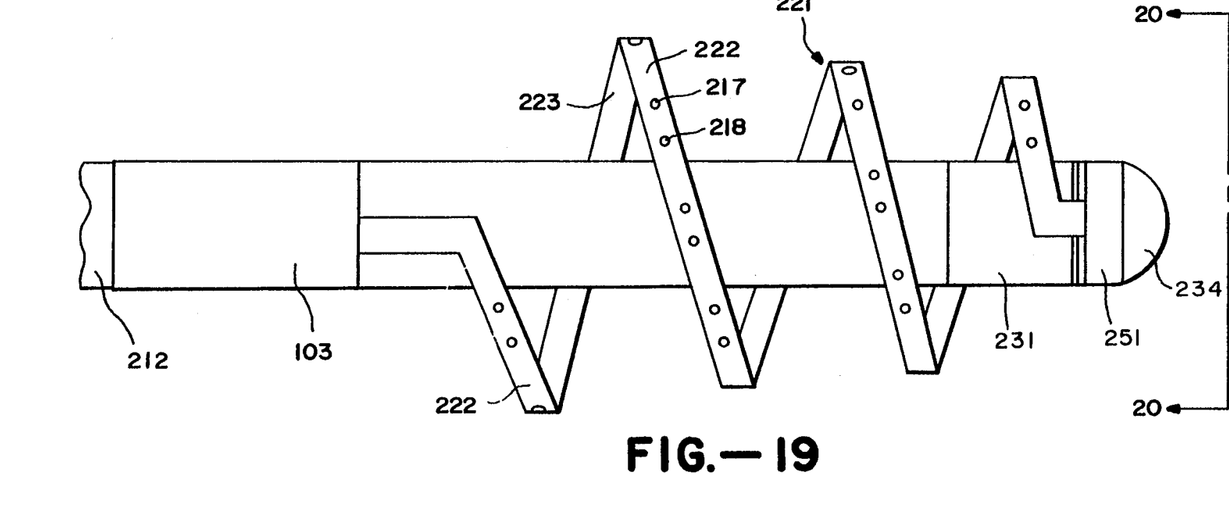
FIG. 19 is a partial elevational view showing the catheter probe of FIG. 16 with the expandable means in an expanded position.

A plurality of longitudinally and radially spaced apart sets 216 of bipolar electrodes 217 and 218 are provided beyond the distal extremity of the flexible elongate tubular member 36. Expandable means is secured to the distal extremity of the flexible elongate tubular member 36 for carrying and supporting the sets 216 of electrodes 217 and 218. In the embodiment shown in FIGS. 16–20, the expandable means takes the form of a single flexible elongate strip or element 221 formed of a suitable material such as the plastic utilized for the arms 47 in the hereinbefore described embodiment of the present invention. The single flexible elongate strip 221 is utilized which is wrapped in a spiral fashion and is movable between contracted and expanded positions. The contracted position is shown in FIG. 16 and an expanded position is shown in FIG. 19.

The flexible elongate strip 221 is provided with an outer surface 222 and an inner surface 223. The sets of electrodes 216 can be formed as multilayer electrodes 217 and 218 on the outer surface 222 in the manner hereinbefore described for the previous embodiment and can have generally the same size and shape. Leads (not shown) can also be formed on the inner surface 223 in a manner similar to that hereinbefore described. The bipolar pairs of electrodes 217 and 218 are disposed longitudinally of the strip 221 or in other words in a helical direction as shown. If desired, the bipolar pairs of electrodes 217 and 218 can be arranged in different manners on the strip. For example, they can be staggered so that they extend in a direction which is at right angles to the longitudinal axis of the flexible elongate member 36.

It should be appreciated that if it is desired to achieve improved voltage propagation between the bipolar electrodes, a concentric arrangement of the bipolar electrodes can be utilized. As shown in FIG. 21, each set 226 of bipolar electrodes 227 and 228 has the electrode 227 is the form of a circular disc and electrode 228 as an annulus disposed coaxially with respect to the disc 227. The electrodes 227 and 228 can be multilayered as the electrodes 67 and 68 hereinbefore described. By way of example, the electrode 227 can have a diameter of 0.030", the space between the electrode 227 and the ring electrode 228 0.030" with the ring electrode 228 having a width of approximately 0.010". The sets 226 of electrodes 227 and 228 can be spaced lengthwise of the flexible elongate strip 221 so that they are spaced apart radially and longitudinally when the flexible elongate strip 221 is wrapped in the spiral manner shown in FIG. 16.

Figure 17:
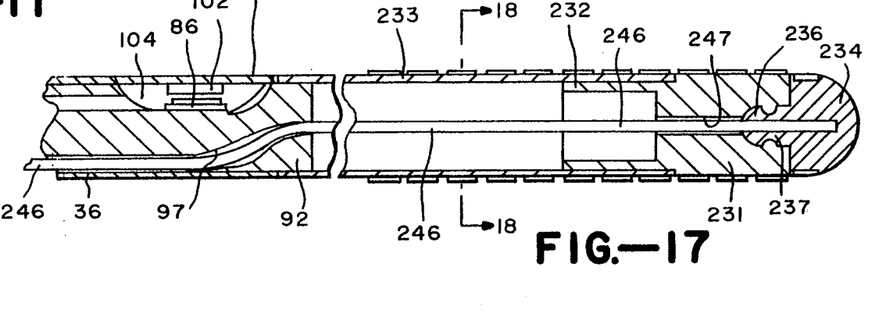
FIG. 17 is a cross sectional view taken along the line 17—17 of FIG. 16.

Means is provided for moving the expandable means expanded between expanded and contracted positions and consists of an elongate cylindrical tubular member 231 formed of a suitable material such as plastic having an annular recess 232 at the proximal extremity thereof, a plastic tube 233 formed of a heat-shrinkable material is shrunk over the proximal extremity of the tubular member 231 and is seated within the recess 232. It is also shrunk over the distal extremity of the mandrel 92 to secure the tubular member 231 to the mandrel 92. Another plastic or metal cylindrical tubular member 234 is provided in the form of a rounded tip. Cooperative means is provided for rotatably mounting the cylindrical tubular member 234 on the distal extremity of the cylindrical member 231 and consists of a female recess 236 formed in distal extremity of the cylindrical member 231 which is adapted to receive by a snap-in fit a male protrusion 237 on the tip member. Thus, it can be seen that there can be relative rotation between the cylindrical member 231 and the cylindrical member 234 while restraining longitudinal movement between the same.

Means is provided for rotating the tip member 234 with respect to the distal extremity of the cylindrical member 231 and consists of a torque element or wire 246 which extends from the proximal extremity of the flexible elongate tubular member 36 through the hole 97 of the mandrel 92 and through a hole 247 in the cylindrical member 231 and is coupled to the tip member 234 by extending into a hole 248 in the tip member 234 and bonded therein by suitable means such as solder or an adhesive.

One of the ends of the flexible elongate strip 221 is secured to the distal extremity of the tip member 234 by suitable means such a band 251 and an adhesive. Similarly the other of the ends of the flexible elongate strip 221 is secured to the distal extremity of the mandrel 92 in a suitable manner such as clamping it under the cover 103. The torque wire 246 can be connected to the knob 117 hereinbefore described which can be utilized for rotating the torque wire 246 rather than controlling the pull wire as in the previous embodiment.

The flexible elongate strip 221 is wound on the tubular member 231 in a clockwise direction and is relatively tightly wrapped as shown in FIG. 16 to assume its contracted position. The flexible elongate strip 221 can be moved to an expanded position by rotation of the torque element or wire 246 and the tip member 234 secured thereto in a counterclockwise direction to cause the turns of the helix of the flexible strip 221 to gradually expand in a circumferential direction to an expanded position simulating a position such as that shown in FIG. 19, that it would assume within a chamber of the heart and to move the electrodes 217 and 218 carried thereby into engagement with the wall forming the chamber of the heart in which the expandable means is disposed.

The leads (not shown) on the inner surface 223 are connected to a multiplexer chip 86 provided in the distal extremity of the flexible elongate member 36 in the same manner as heretobefore described in connection with the previous embodiment. The multiplexer 86 is connected by leads to the interface module 29 and to the computer 31 in the same manner as the previously described embodiment.

The catheter probe 211 of the embodiment shown in FIG. 16-20 can be readily introduced into a chamber of the heart in the same manner as the embodiment of the catheter probe hereinbefore described. As soon as the distal extremity of the catheter or probe 211 is positioned within the desired cavity of the heart, the knob 121 can be rotated in the appropriate direction to cause unwinding of the spirally wrapped flexible elongate strip 221 to cause it to progressively enlarge. Rotation is continued until the enlargement is sufficient to bring the electrodes 217 and 218 carried thereby into engagement with the wall of the heart forming the chamber in which the distal extremity of the catheter or probe 211 is disposed. By applying additional rotational forces to the knob 117, the size of the spiral formed by the flexible elongate strip 221 can be increased until all or substantially all of the electrodes carried by the strip 221 are moved into engagement with the wall. Since the strip 221 is flexible, the heart can continue its normal beating pattern in moving the wall forming the chamber inwardly and outwardly. At the same time, the spacing provided between the turns of the spiral formed by the flexible elongate strip 221 permits normal substantially unimpeded blood flow in the chamber in which the catheter probe 211 is located. The springiness of the flexible elongate strip 221 permits the flexible elongate element or strip 221 to follow the muscular contractions and expansions of the heart while still maintaining the electrodes in continuous contact with the heart wall and in contact with electrical circuitry provided within the heart wall.

When the desired potential measurements have been made which will give potentials extending around the 360° of the chamber, additional potential measurements can be made by partially contracting the spirally wound flexible elongate strips 221 by rotation of the knob 117 in an opposite direction the distal extremity of the probe 211 can be rotated through a desired angle, as for example, 15°. The flexible elongate strip 221 can then again be moved to an expanded position into engagement with the heart wall and additional potential measurements made.

If thereafter, it is desired to carry out an ablation step, this can be accomplished in the manner hereinbefore described by providing a high voltage between a selected set of bipolar electrodes.

Thereafter, after the desired procedures have been carried out, the catheter probe 211 can be removed from the body by operating the knob 117 to move the flexible elongate strip 221 into its contracted position helically wrapped about the tubular member 231. The entire catheter probe 211 can then be removed in a conventional manner.

It should be appreciated that rather than providing a single flexible elongate element or strip 221, a plurality of such flexible elements or strips can be provided which are disposed adjacent to each other to form a plurality of helices. The helices can be wound into a plurality of abutting or nearly abutting helices which can be expanded and contracted in the same manner as a single helix formed from a single flexible elongate member strip 221.

From the foregoing, it can be seen that several embodiments of the present invention have been provided which can be utilized for carrying out endocardial mapping and ablation. All of the embodiments make possible the making of simultaneous measurements at many portions of the wall forming the chamber of the heart in which the catheter probe is disposed, making it possible to make simultaneous potential measurements from such portions extending through 360°. Thus, it is possible to map the entire heart wall forming the chamber in a single step without the necessity of rotating the catheter probe to several rotational positions which may be very time consuming. In addition, with such different positions it may be difficult to precisely ascertain where the measurements were made in the chamber of the heart.

All of the embodiments of the invention have the advantage that during operation of the probe within the chamber, the heart can continue its normal operation with substantially unimpeded blood flow in the chamber because of the spacing provided between expandable means carrying the electrodes.

What is claimed is:

1. A method for forming a flexible cylindrical member for use with a catheter probe, comprising providing a generally rectangular sheet of flexible insulating material having a predetermined length and width with opposite sides extending along the length and opposite sides extending across the width, forming first and second end portions on each of the two opposite sides of the length of the sheet, placing a plurality of parallel slits in the sheet extending along the length from said end portions in directions generally perpendicular to the end portions to provide a plurality of laterally spaced apart arms extending longitudinally parallel to the slits between said end portions, providing a plurality of spaced apart electrodes on each of said arms, providing leads carried by said arms in contact with said electrodes, wrapping the sheet into a cylindrical shape, securing said first and second end portions circumferentially on each side to retain said cylindrical shape and to form a cylindrical member having proximal and distal extremities with the arms being substantially equally distributed around the circumference of the cylindrical member and causing the arms to be bowed outwardly by moving the proximal extremity of the cylindrical member relative to the distal extremity of the cylindrical member in a longitudinal direction parallel to the slits thereby bringing the proximal and distal extremities of the cylindrical member closer to each other in predetermined relative positions thereof, securing said proximal and distal extremities in said predetermined position to thereby retain the arms so that they are outwardly bowed, producing the flexible cylindrical member for use with the catheter probe.

2. A method as in claim 1 together with the step of providing spring material in the insulating material to provide springiness in the arms.

3. A method for forming a flexible expandable member for use with a catheter probe, comprising providing a flexible elongate member having first and second portions, providing a flexible elongate element of insulating material having an outer surface and first and second ends, forming a plurality of spaced apart electrodes on the element, wrapping said element into a helix onto said flexible elongate member by moving one end of the element with respect to the other end of the element in one circumferential direction and securing said first and second end portions in spaced apart positions on opposite ends of the helix on said first and second portions of the flexible elongate member to provide a flexible expandable member of cylindrical shape with the outer surface facing outwardly and rotating one end of the flexible elongate element with respect to the other end of the flexible elongate element in an opposite circumferential direction by relative rotation of said first and second portions of said flexible elongate member with respect to each other to cause the helix to expand to move the electrodes carried thereby in an outward direction.

* * * * *